US006191144B1

(12) United States Patent
Isner

(10) Patent No.: US 6,191,144 B1
(45) Date of Patent: Feb. 20, 2001

(54) METHOD OF USING ANGIOTENSIN CONVERTING ENZYME INHIBITOR TO STIMULATE ANGIOGENESIS

(75) Inventor: Jeffrey Michael Isner, Weston, MA (US)

(73) Assignee: Warner-Lambert Company, Morris Plains, NJ (US)

(*) Notice: Under 35 U.S.C. 154(b), the term of this patent shall be extended for 0 days.

(21) Appl. No.: 09/361,351

(22) Filed: Jul. 26, 1999

Related U.S. Application Data

(60) Provisional application No. 60/096,814, filed on Aug. 17, 1998.

(51) Int. Cl.[7] .................................................. A61K 31/445

(52) U.S. Cl. ............... 514/315; 514/213.01; 514/217.11; 514/299; 514/307; 514/330

(58) Field of Search .................................... 514/315, 330, 514/299, 307, 213.01, 217.11

(56) References Cited

U.S. PATENT DOCUMENTS

| 4,344,949 | 8/1982 | Hoefle et al. | 424/258 |
|---|---|---|---|
| 4,374,829 | 2/1983 | Harris et al. | 424/177 |
| 4,425,355 | 1/1984 | Hoefle et al. | 424/274 |
| 5,166,143 | * 11/1992 | Ondetti et al. | 514/89 |
| 5,231,080 | * 7/1993 | Scholkens | 514/2 |

OTHER PUBLICATIONS

Takeshita S., et al., "Therapeutic Angiogenesis A Single Intraarterial Bolus of Vascular Endothelial Growth Factor Augments Revascularization in a Rabbit Ischemic Hind Limb Model", *J. Clin. Invest.*, vol. 93, Feb. 1994, pp 662–670.
Fabre J., et al., "Angiotensin Converting Enzyme Inhibition With Quinaprilate Stimulates Angiogenesis in a Rabbit Model of Hindlimb Ischemia", *Am. J. Cardiol.*, vol. 31, No. 2, Feb. 1998, p 239A.
J. M. Isner, "Angiogenesis for Revascularization of Ischaemic Tissues", *Eur. Heart J.*, vol. 18, Jan. 1997, pp 1–2.
Stoll M., et al., "The Angiotensin AT2–Receptor Mediates Inhibition of Cell Proliferation in Coronary Endothelial Cells", *J. Clin. Invest.*, vol. 95, Feb. 1995, pp 651–657.
Mancini G. B., et al., "Angiotensin–Converting Enzyme Inhibition With Quinapril Improves Endothelial Vasomotor Dysfunction in Patients With Coronary Artery Disease", *Circulation*, vol. 94, 1996 pp 258–265.
Rakugi H., et al., "Vascular Injury Induces Angiotensinogen Gene Expression in the Media and Neointima", *Circulation*, vol. 87, No. 1, Jan. 1993, pp 283–290.
Naftilan A. J., et al., "Localization and Differential Regulation of Angiotensinogen mRNA Expression in the Vessel Wall", *J. Clin. Invest.*, vol. 87, Apr. 1991, pp 1300–1311.
Caldwell P., et al., "Angiotensin–Converting Enzyme: Vascular Endothelial Localization", *Science*, vol. 191, Mar. 12, 1976, pp 1050–1051.

VanLeeuwen R., et al., "Angiotensin II Increases Plasminogen Activator Inhibitor Type 1 and Tissue–Type Plasminogen Activator Messenger RNA in Cultured Rat Aortic Smooth Muscle Cells", *Circulation*, vol. 90, No. 1, Jul. 1994, pp 362–368.
Diet F., et al., "Increased Accumulation of Tissue ACE in Human Atherosclerotic Coronary Artery Disease", *Circulation*, vol. 94, 1996, pp 2756–2767.
Victor J. Dzau, "Molecular and Physiological Aspects of Tissue Renin–Angiotensin System: Emphasis on Cardiovascular Control", *J. Hypertens.*, vol. 6, No. 3, 1988, pp S7–S12.
Peters K., et al., "Vasopressin and the Mature Coronary Collateral Circulation", *Circulation*, vol. 79, No. 6, Jun. 1989, pp 1324–1331.
Yang H. T., et al., "Angiotensin–Converting Enzyme Inhibition Increases Collateral–Dependent Muscle Blood Flow", *J. Appl. Physiol.*, vol. 75, 1993, pp 452–457.
Ziada A., et al., "The Effect of Long–Term Vasodilation on Capillary Growth and Performance in Rabbit Heart and Skeletal Muscle", *Cardiovascular Research*, vol. 18, 1984, pp 724–732.
Andrade S. P., et al., "Inhibitors of Nitric Oxide Synthase Selectively Reduce Flow in Tumor–Associated Neovasculature", *Br. J. Pharmacol*, vol. 107, 1992, pp 1092–1095.
Ziche M., et al., "Nitric Oxide Mediates Angiogenesis In Vivo and Endothelial Cell Growth and Migration In Vitro Promoted by Substance P", *J. Clin. Invest.*, vol. 94, Nov. 1994, pp 2036–2044.
Munzenmaier D. H., et al., "Opposing Actions of Angiotensin II on Microvascular Growth and Arterial Blood Pressure", *Hypertension*, vol. 27, 1996, pp 760–765.
Le Noble F. A., et al., "Evidence for a Novel Angiotensin II Receptor Involved in Angiogenesis in Chick Embryo Chorioallantoic Membrane", *Am. J. Physiol.*, vol. 264, 1993, pp R460–R465.
Cameron N. E., et al., "angiotensin Converting Enzyme Inhibition Prevents Development of Muscle and Nerve Dysfunction and Stimulates Angiogensis in Streptozotocin–Diabetic Rats", *Diabetologia*, vol. 35, 1992, pp 12–18.

(List continued on next page.)

*Primary Examiner*—Frederick Krass
(74) *Attorney, Agent, or Firm*—Michael J. Aktins

(57) ABSTRACT

The present invention is directed to the use of a group of ACE inhibitors to stimulate angiogenesis in mammals or in mammalian tissue in vitro. Specifically, the present invention is directed to inducing or enhancing angiogenesis through the administration of a group of ACE inhibitors and to ACE inhibitor-containing compositions for effecting the inducement or enhancement of angiogenesis. The ACE inhibitors may also be useful in the promotion of angiogenesis, such as in the promotion of wound healing, bone healing, and in the treatment of bums, as well as in promoting the formation, maintenance, and repair of tissue. In a preferred embodiment, the ACE inhibitor, quinapril, or quinaprilat, is used to treat, prophalactically or otherwise, mammals in need of angiogenic-treatment.

17 Claims, 11 Drawing Sheets

OTHER PUBLICATIONS

Maxfield E. K., et al., "Angiotensin II Receptor Blockade and Nerve Function, Modulates Nerve Blood Flow and Stimulates Endoneurial Angiogenesis in Streptozotocin–Diabetic Ratsand Nerve Function", *Diabetologia*, vol. 36,1993, pp 1230–1237.

Olivetti G., et al., "Spirapril Prevents Left Ventricular Hypertrophy, Decreases Myocardial Damage and Promotes Angiogenesis in Spontaneously Hypertensive Rats", *J. Cardiovasc, Pharmacol.*, vol. 21, No. 3, 1993, pp 362–370.

Clozel J. P., et al., "Effects of Chronic ACE Inhibition on Cardiac Hypertrophy and Coronary Vascular Reserve in Spontaneously Hypertensive Rats With Developed Hypertension", *J. Hypertens.*, vol. 7, 1989, pp 267–275.

Gohlke P., et al., "Blockade of Bradykinin $B_2$ Receptors Prevents the Increase in Capillary Density Induced by Chronic Angiotensin–Converting Enzyme Inhibitor Treatment in Stroke–Prone Spontaneously Hypertensive Rats", *Hypertension*, vol. 29, No. 1, Jan. 1997, pp 478–482.

O'Driscoll G., et al., "Improvement in Endothelial Function by Angiotensin Converting Enzyme Inhibition in Insulin–dependent Diabetes Mellitus", *J. Clin. Invest.*, vol. 100, No. 3, Aug. 1997, pp 678–684.

Fabris B., et al., "Inhibition of Angiotensin–Converting Enzyme (ACE) in Plasma and Tissue", *J. Cardiovasc. Pharmacol.*, vol. 15, Suppl. 2, 1990, pp S6–S13.

Prens E., et al., "Nephrotic Syndrome in Patient on Captopril", *Lancet*, vol. 2, Aug. 1979, pp 306–307.

Gavras I., et al., "Fatal Pancytopenia Associated with the Use of Captopril," *Ann. Intern. Med.*, vol. 94, No. 1, Jan. 1981, pp 58–59.

Volpert O., et al, "Captopril Inhibits Angiogenesis and Slows the Growth of Experimental Tumores in Rats", *J. Clin. Invest.*, vol. 98, No. 3, Aug. 1996, pp 671–679.

Williams B., et al., "Angiotensin II Increases Vascular Permeability Factor Gene Expression by Human Vascular Smooth Muscle Cells", *Hypertension*, vol. 25, 1995, pp 913–917.

Schaper W., et al., "Molecular Mechanisms of Coronary Collateral Vessel Growth", *Circulation Research*, vol. 79, 1996, pp 911–919.

Van Belle E. et al., "ACE Inhibition Accelerates Endothelial Regrowth in Vivo: A Possible Explanation for the Benefit Observed with ACE Inhibitiors Following Arterial Injury", *Biochem. Biophys. Res. Comm.*, vol. 231, 1997, pp 577–581.

Warren J., et al., "Captopril Increases Skin Microvascular Blood Flow Secondary to Bradykinin, Nitric Oxide, and Prostaglandins", *Faseb J.*, vol. 9, Mar. 1995, pp 411–418.

Gohlke P., et al., "Long–Term Low–Dose Angiotensin Converting Enzyme Inhibitor Treatment Increases Vascular Cyclic Guanosine 3', 5'–Monophosphate", *Hypertension*, vol. 22, No. 5, Nov. 1993, pp 682–687.

Zhang X., et al., "ACE Inhibitors Promote Nitric Oxide Accumulation to Modulate Myocardial Oxygen Consumption", *Circulation*, vol. 95, 1997, pp 176–182.

Van Belle E., et al., "No Synthesis is Involved in Structural and Functional Effects of ACE Inhibitors in Injured Arteries", *Am. J. Physiol.*, vol. 270 (1 Pt 2), pp H298–H305, 1997.

Ziche M., et al., "Nitric Oxide Synthase Lies Downstream from Vascular Endothelial Growth Factor–Induced but Not Basic Fibroblast Growth Factor–Induced Angiogenesis", *J. Clin. Invest.*, vol. 99, No. 11, Jun. 1997, pp 2625–2634.

Ziche M., et al., "Nitric Oxide Promotes Proliferation and Plasminogen Activator Production by Coronary Venular Endothelium Through Endogenous bFGF", *Circulation Research*, vol. 80, 1997, pp 845–852.

* cited by examiner

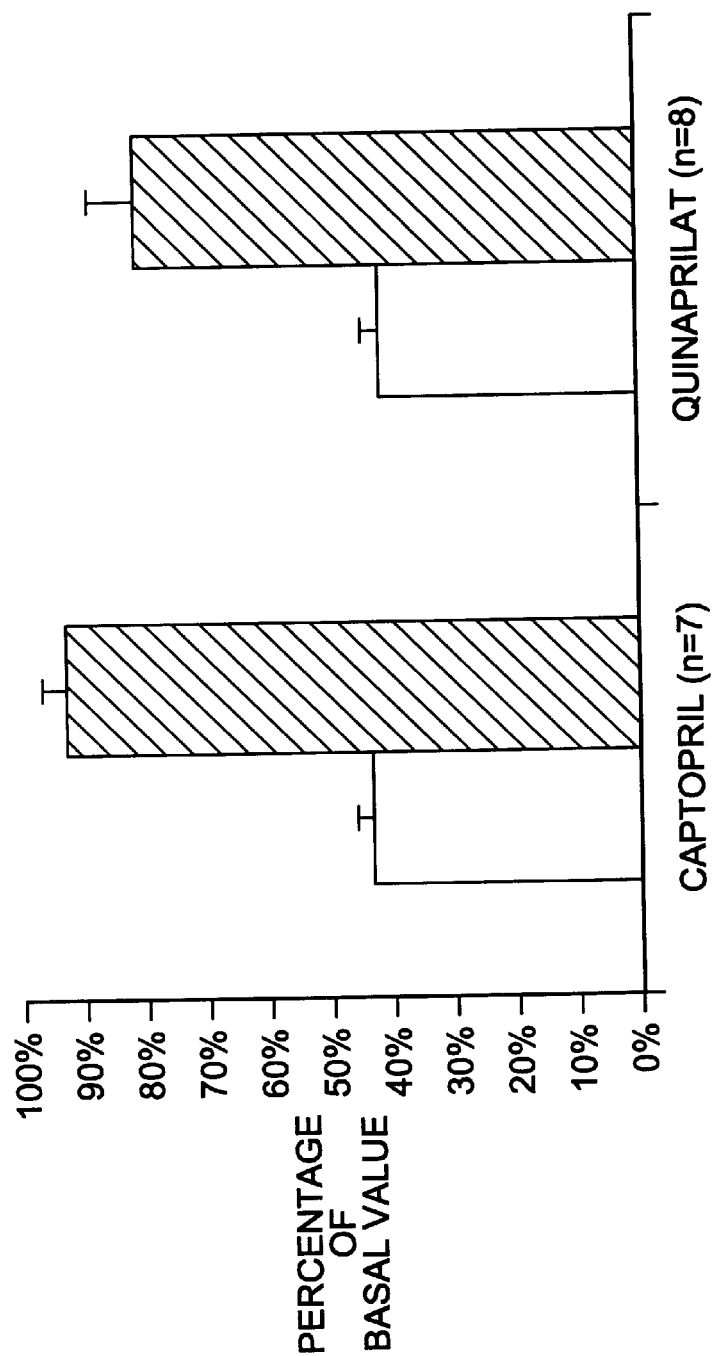
FIG-1A ACE PLASMA ACTIVITY

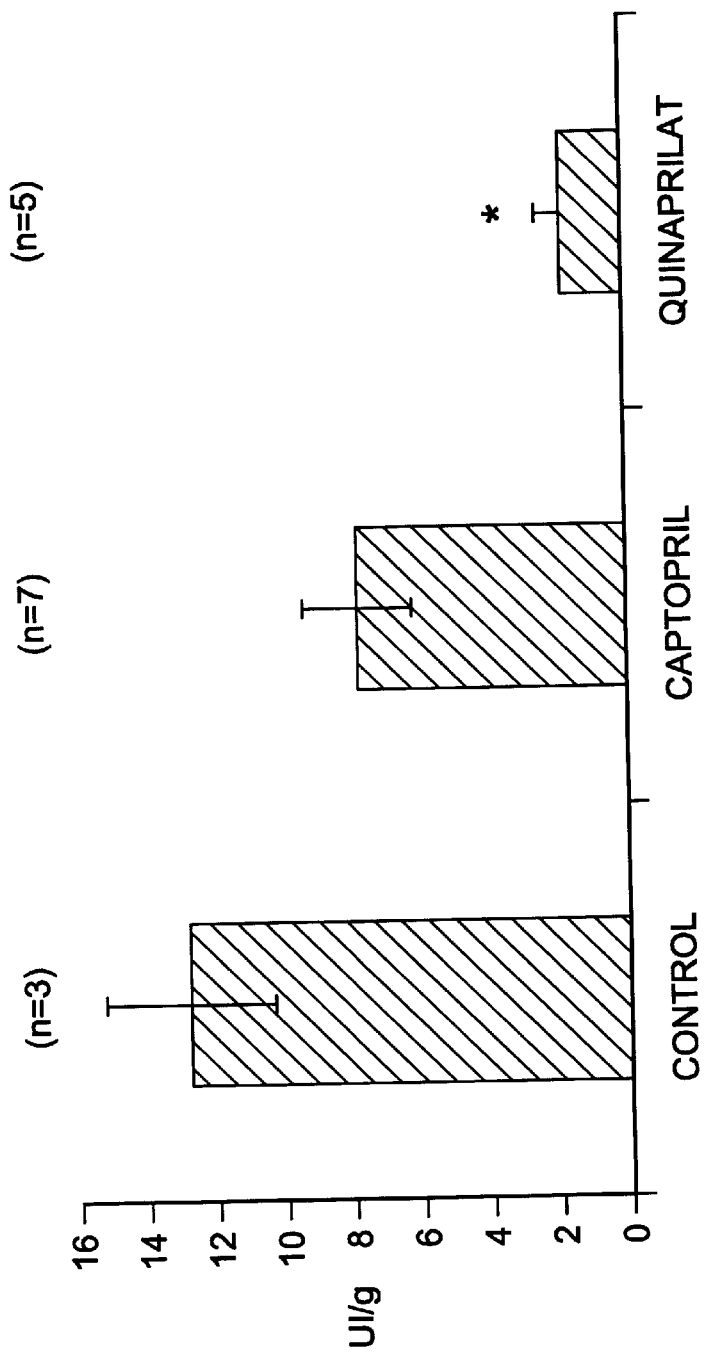
FIG-1B  ACE TISSUE ACTIVITY

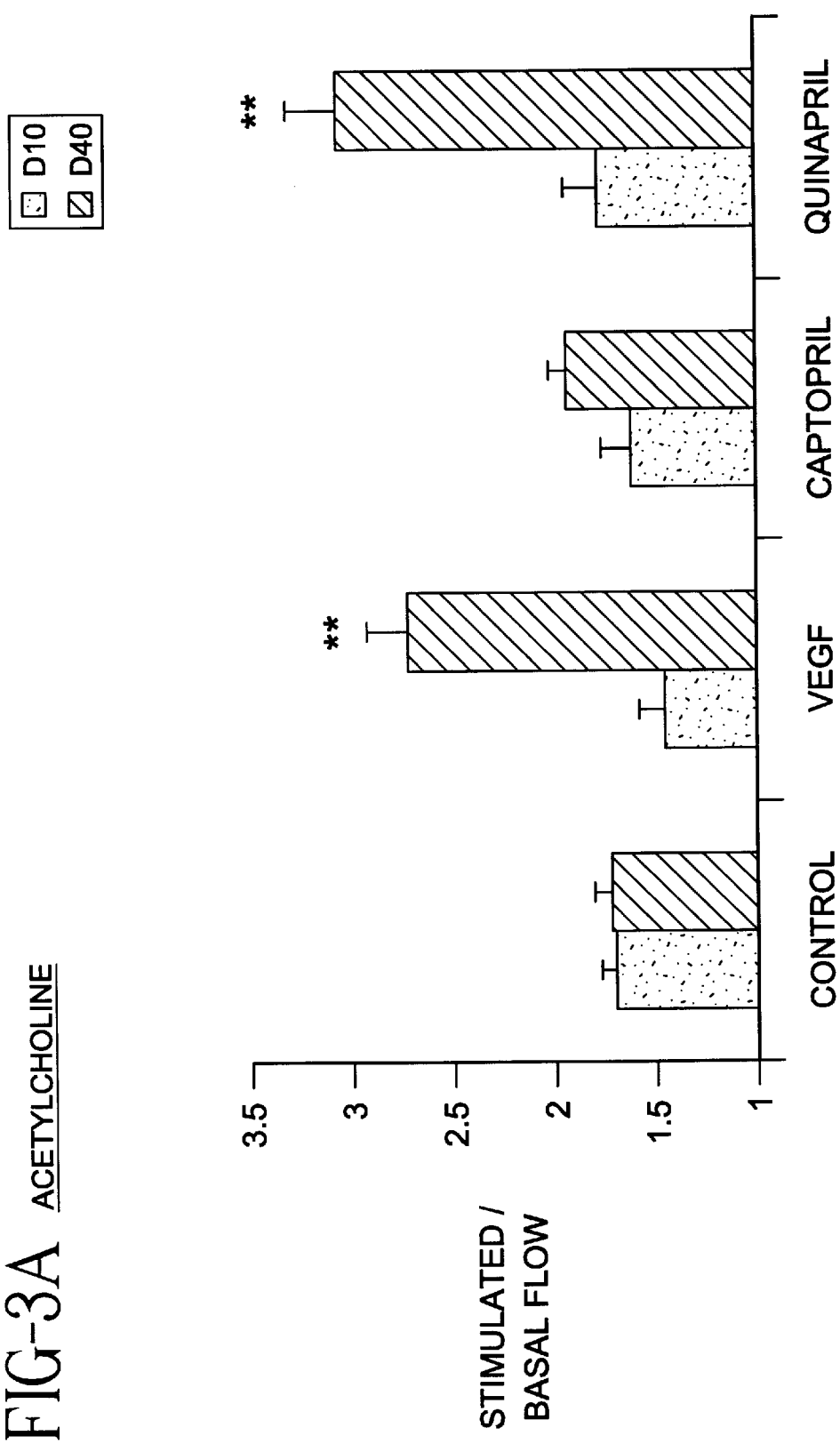
FIG-3A ACETYLCHOLINE

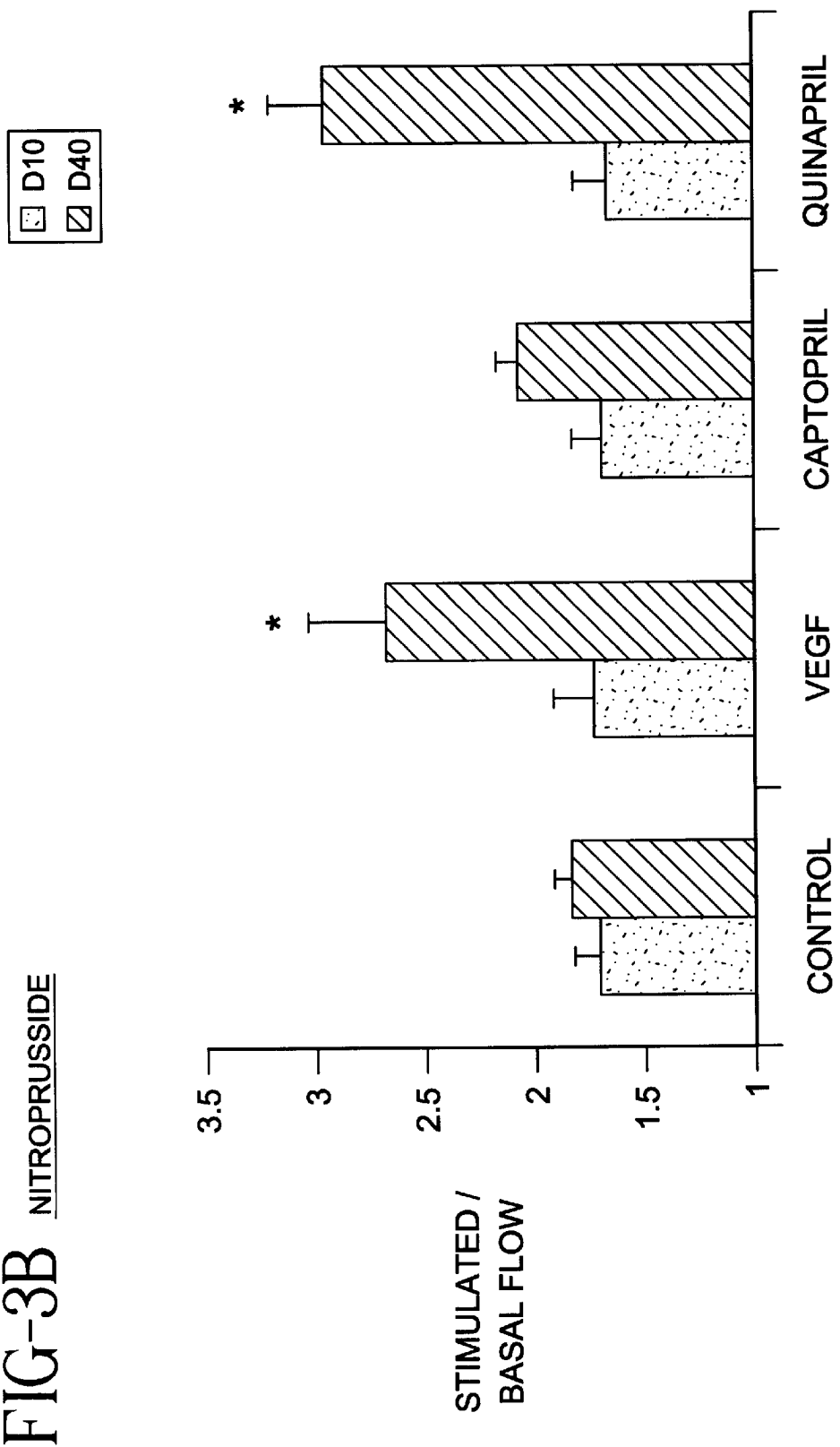
FIG-3B NITROPRUSSIDE

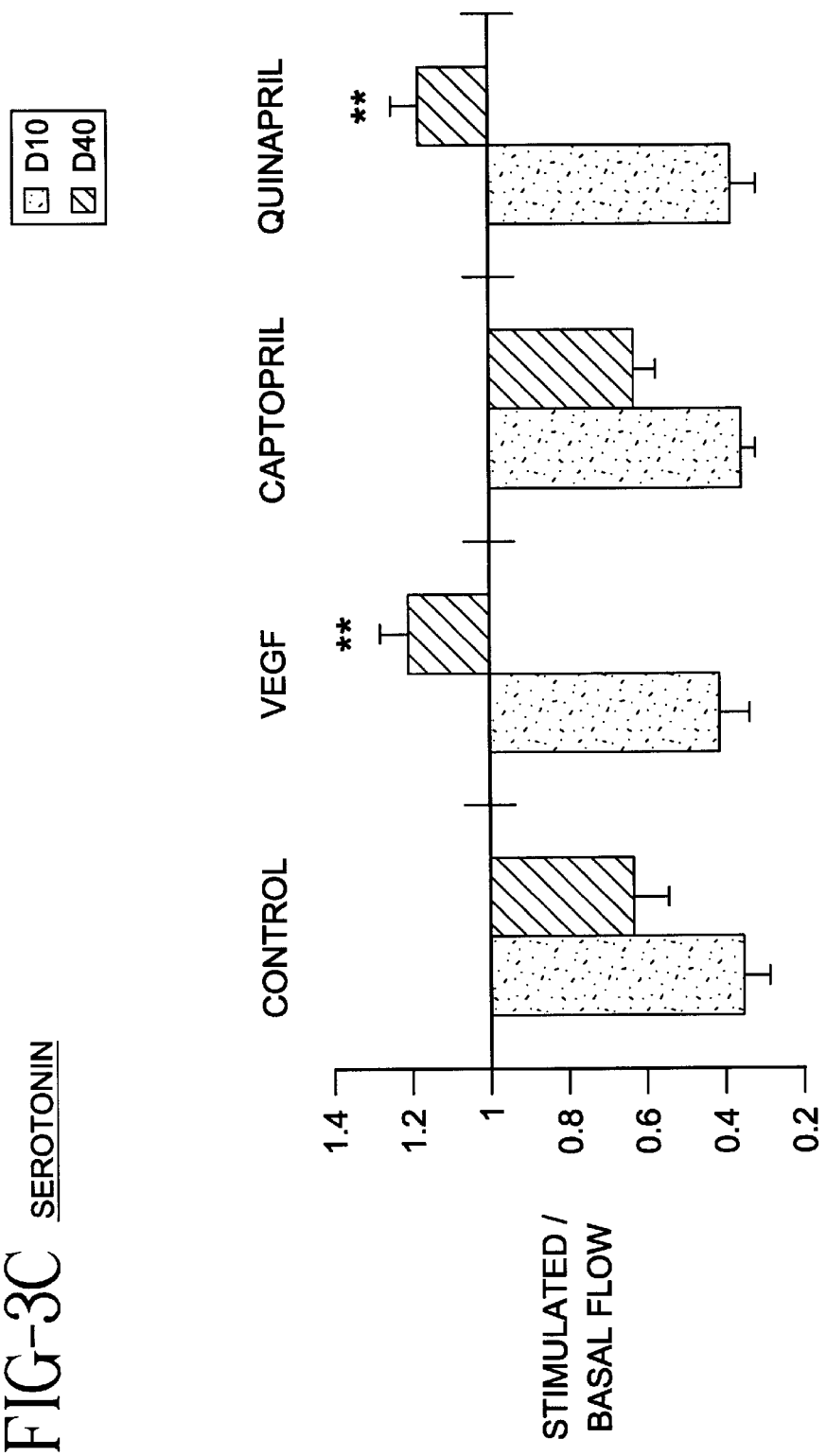
FIG-3C SEROTONIN

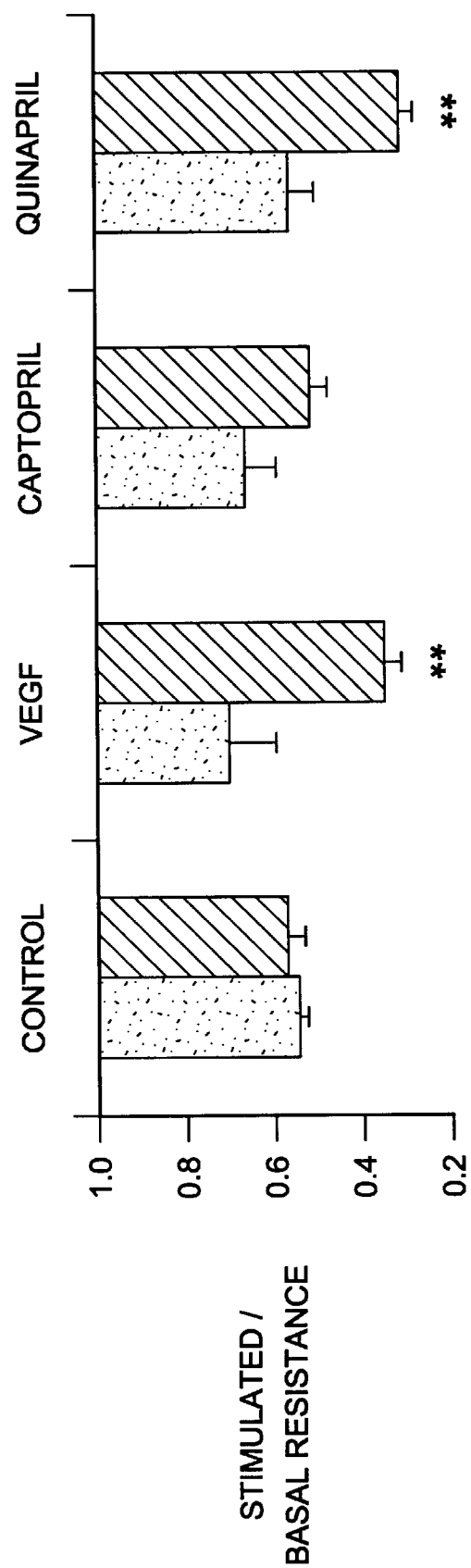
FIG-4A ACETYLCHOLINE

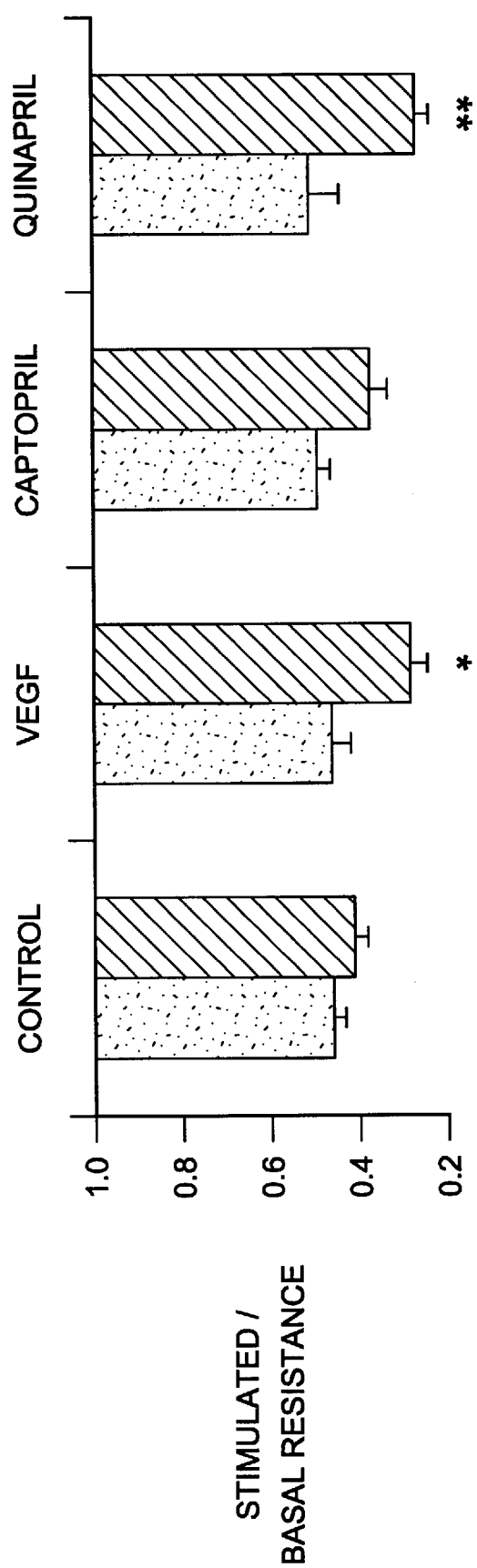
FIG-4B NITROPRUSSIDE

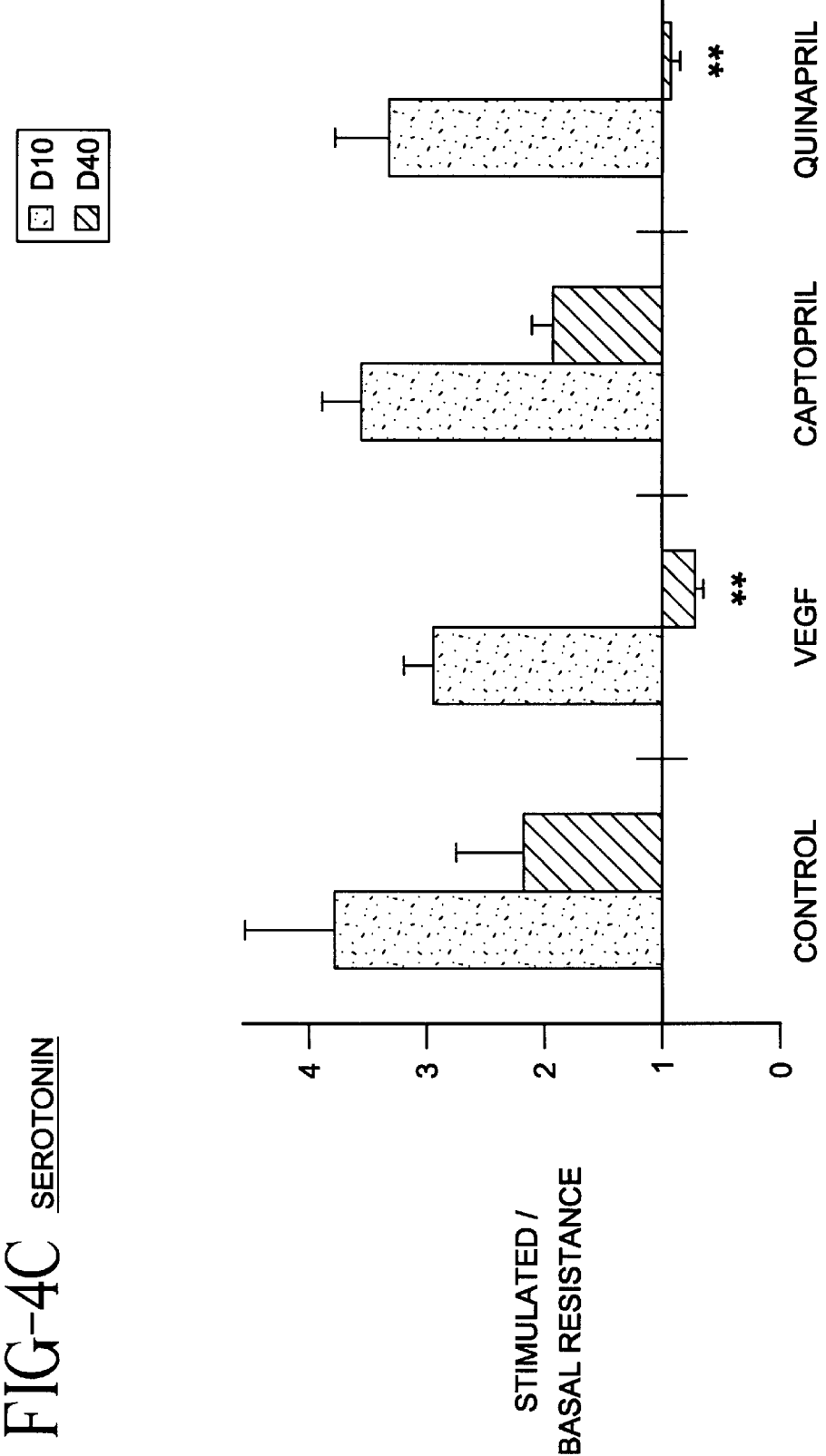
FIG-4C SEROTONIN

METHOD OF USING ANGIOTENSIN CONVERTING ENZYME INHIBITOR TO STIMULATE ANGIOGENESIS

This application claims the benefit of U.S. Provisional Application Ser. No. 60/096,814 filed Aug. 17, 1998.

FIELD OF THE INVENTION

The present invention is directed to the use of a group of ACE inhibitors to stimulate angiogenesis in mammals or in mammalian tissue in vitro. Specifically, the present invention is directed to inducing or enhancing angiogenesis through the administration of a group of ACE inhibitors and to ACE inhibitor-containing compositions for effecting the inducement or enhancement of angiogenesis. The ACE inhibitors may also be useful in the promotion of angiogenesis, such as in the promotion of wound healing, bone healing, and in the treatment of burns, as well as in promoting the formation, maintenance, and repair of tissue. In a preferred embodiment, the ACE inhibitor, quinapril, or quinaprilat, is used to treat, prophalactically or otherwise, mammals in need of angiogenic treatment.

BACKGROUND OF THE INVENTION

Angiogenesis refers to the growth of new blood vessels, or "neovascularization," and involves the growth of capillaries composed of endothelial cells. Angiogenesis is an integral part of many important biological processes, and may aid in the healing of wounds and fractures, the vascularizing of synthetic skin grafts, and the enhancement of collateral circulation where there has been vascular occlusion or stenosis. New blood vessel formation is required for the development of any new tissue, whether normal or pathological, and thus represents a potential control point in regulating many disease states, as well as a therapeutic opportunity for encouragement of the growth of normal tissue.

The complete process of angiogenesis is not entirely understood, but it is known to involve the endothelial cells of the capillaries. Endothelial cells line the walls of blood vessels, and capillaries are comprised almost entirely of endothelial cells. The angiogenic process comprises a cascade of events, including protease secretion by endothelial cells, degradation of the basement membrane, migration through the surrounding matrix, proliferation, alignment, differentiation into tube-like structures, and synthesis of a new basement membrane.

A number of factors are well-known in the art to stimulate angiogenesis. Many of these are peptide factors, and the most notable among these are fibroblast growth factors, epidermal growth factors, vascular endothelial growth factors, insulin-like growth factors, transforming growth factors, platelet-derived growth factor, and interleukins. Other factors which are known to show angiogenic-stimulating activity, but which are not proteins, include prostaglandins E1 and E2, fragments of hyaluronic acid and nicctinamine. However, the therapeutic applicability of some of these compounds, especially as systemic agents, is limited by their potent pleiotropic effects on various cell types. There remains a need, therefore, for an angiogenic agent with more general applicability.

BRIEF DESCRIPTION OF THE DRAWINGS

FIG. 1. Bar graphs of measured ACE activity. Values are mean +SEM. FIG. 1 (A): ACE activity in plasma expressed as the percentage of the basal value measured before any treatment, after the fourth first days of treatment (D14), and after 5 days of discontinuation (D40). The ACE inhibition was equivalent in both groups at D14, and both groups have recovered an ACE activity close to basal value at D40; differences are not significant. FIG. 1 (B): ACE activity per gram of muscle tissue (UI/g) in 15 additional rabbits; the intergroup difference (ANOVA: $p<0.01$) is the expression of a significant difference in magnitude of inhibition with quinaprilat compared to the control rabbits (*=$p<0.05$).

FIG. 3. Bar graphs (FIGS. 3A, 3B and 3C) of the blood flow change in internal iliac artery, responding to endothelium-dependent and -independent agents at D10 and D40. Values are means ±SEM. At D40, acetylcholine and nitroprusside responses remain moderate in control and captopril groups, whereas responses in VEGF or quinaprilat treated animals disclosed a significantly higher increase in blood flow. The same pattern of responses was obtained with serotonin, that is the reduction in blood flow was significantly less severe in VEGF or quinaprilat groups than that observed in control animals at D40. This chart shows a higher collateral reactivity, comparable to VEGF one, with only one of the two tested ACE inhibitors, suggesting that this hemodynamic amelioration with quinaprilat reflects an anatomical extension of the vascular network (*=$p<0.05$, **=$p<0.01$)

FIG. 4. Bar graphs (FIGS. 4A, 4B and 4C) of the resistance change in internal iliac artery, responding to endothelium-dependent and -independent agents at D10 and D40. Values are means +SEM. After acetylcholine and nitroprusside stimulation at D40, resistance response in VEGF- or quinaprilat-treated animals developed a franker diminution than in control and captopril groups. Serotonin elicited the same response profile, dissociating VEGF or quinaprilat groups from control and captopril animals in the magnitude of resistance decrease at D40. This chart discloses a modification in resistance profile with only one of the two tested ACE inhibitors, in the same range as VEGF-treated rabbits, suggesting that this hemodynamic amelioration with quinaprilat reflects an anatomical extension of the vascular network (*=$p<0.05$, **=$p<0.01$).

SUMMARY OF THE INVENTION

Figure 2:
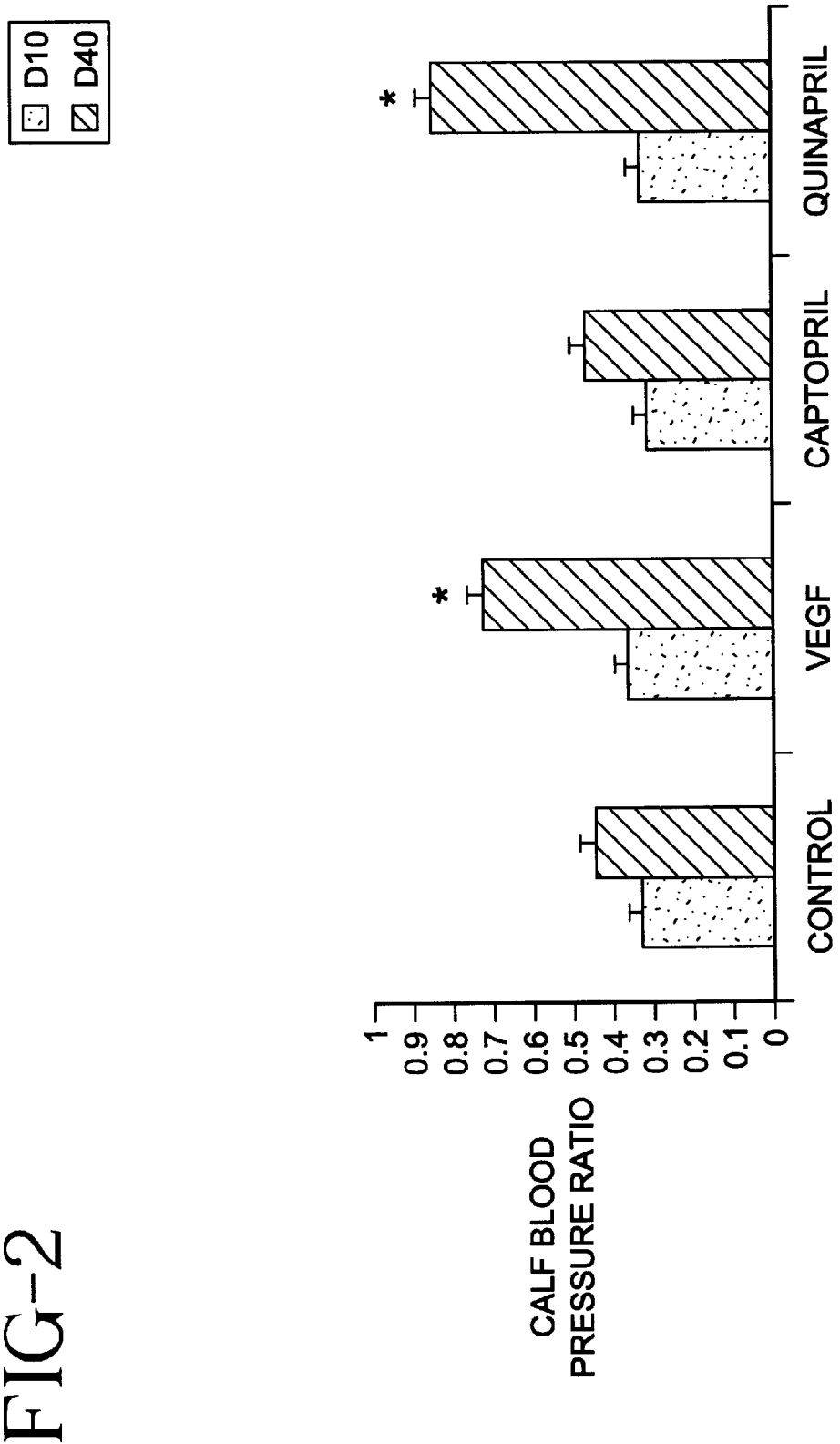
FIG. 2. Bar graph of the systolic blood pressure ratio of ischemic hindlimb to healthy hindlimb. Values are mean ±SEM. ANOVA test displayed a significant difference between the four groups ($p<0.01$), and the group to group comparison showed a significantly higher improvement of the blood pressure ratio in VEGF and quinaprilat groups (*=$p<0.01$) than the ratio in control and captopril groups.

It is an object of the present invention to provide a method of controlling, particularly enhancing, angiogenesis with limited or no adverse effects. It is another object of the present invention to provide a method of treating and preventing diseases and ailments involving angiogenesis such as myocardial and cerebral infarctions, mesenteric or limb ischemia, wounds, and vascular occlusion or stenosis. It is a further object of the present invention to provide a method of treating and healing wounds, bones and burns, as well as in promoting the formation, maintenance and repair of tissue.

These and other advantages of the invention will become apparent from a consideration of the following description of the invention.

It has been surprisingly discovered that a group of ACE inhibitors induce and enhance angiogenesis. The present invention involves stimulating angiogenesis both in vitro and in vivo in mammalian tissue by administering at least one of the group of ACE inhibitors to a mammal or to mammalian tissue in an amount sufficient to stimulate angiogenesis. In a preferred embodiment of the present invention, the ACE inhibitor, quinapril, or quinaprilat, is administered to a mammal or to mammalian tissue in an amount sufficient to stimulate angiogenesis. An advantage of using quinapril or quinaprilat over other known angiogenic agents, many of which have harmful side effects, is that quinapril or quinaprilat have been used for many years to successfully treat humans for hypertension.

DETAILED DESCRIPTION OF THE INVENTION

The present invention is based on the discovery that a group of ACE inhibitors stimulate angiogenesis in mammals and in mammalian tissue. It is to be understood by "stimulate angiogenesis" that the ACE inhibitors either enhance or augment a naturally occurring angiogenic process or, alternatively, induce or initiate an angiogenic process. The extent of development of blood vessels resulting from the angiogenic process so stimulated will vary depending on the specific ACE inhibitor, or combination of ACE inhibitors, that is/are used and the concentration of the inhibitor/s in the regional blood plasma. The present inventive method of stimulating angiogenesis has applicability in both in vitro and in vivo applications.

The ACE inhibitors of the invention, which can be used and administered to mammals in compositions comprising pharmaceutically acceptable ingredients, are compounds conforming to the general formula:

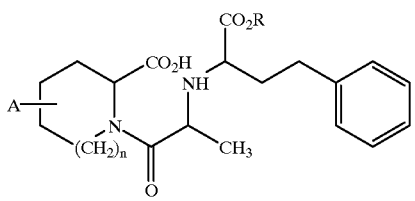

I wherein A is absent, a fused 5-, 6-, or 7-membered cycloaliphatic ring or a fused benzene ring which is unsubstituted or substituted by 1 or 2 alkoxy groups having 1 to 4 carbon atoms; n is 0 or 1, and R is hydrogen or alkyl having 1 to 5 carbon atoms. Preferably A is absent, a fused 5- or 6-membered cycloaliphatic ring or a fused benzene ring which is unsubstituted or substituted by 2 methoxy groups; n is 0 or 1, and R is hydrogen or ethyl.

Particularly valuable are enalapril, quinapril, quinaprilat, or indolapril, their corresponding free acids or pharmaceutically acceptable acid addition or base salts thereof. Compounds of this type are disclosed in U.S. Pat. Nos. 4,344,949, 4,374,829, and 4,425,355, the disclosure of which are hereby incorporated by reference.

The total drug content of the final composition will be about 0.1% to about 70%, preferably from about 0.1% to about 50%, and most preferably from about 0.1% to about 25%.

All percentages stated herein are weight percentages based on total composition weight, unless otherwise stated.

The daily dosages of the pharmaceutical preparations of the invention depend upon the nature of the dosage form, the nature of the drug(s), and the type and extent of any interactive(s) in drug combinations. Thus, the therapeutic needs of the individual patient and the desires of the prescribing physician dictate the dosage levels to be employed. In general, however, the manufacturer's specifications for any drug or drug combination are useful guides to administration. The Physicians' Desk Reference or other suitable publication can be consulted to ascertain appropriate dosage levels.

Nonetheless, typical dosage levels for quinapril and enalapril are from about 1 mg to about 80 mg per dosage.

The ACE inhibitors of the present invention can optionally contain one or more other medicament drugs or beneficial substances. Suitable categories of drugs that may be employed in addition to ACE inhibitors in the instant compositions may vary widely and generally represent any stable drug combination. Illustrative categories and specific examples include:

(a) Diuretics, such as hydrochlorothiazide,
(b) Antitussives, such as dextromethorphan, dextromethorphan hydrobromide, noscapine, carbetapentane citrate, and chlophedianol hydrochloride,
(c) Antihistamines, such as chlorpheniramine maleate, phenindamine tartrate, pyrilamine maleate, doxylamine succinate, and phenyltoloxamine citrate,
(d) Decongestants, such as phenylephedrine hydrochloride, phenylpropanolamine hydrochloride, pseudoephedrine hydrochloride, and ephedrine,
(e) Various alkaloids, such as codeine phosphate, codeine sulfate, and morphine,
(f) Angiogenic agents, such as FGF, VEGF, and the like,
(g) Mineral supplements such as potassium chloride and the like.

The medicaments and/or other beneficial substances to be used herein may be selected from a wide variety of substances and pharmaceutically acceptable forms thereof, e.g., their acid addition salts. Both organic and inorganic salts may be used provided the drug maintains its medicament value. Exemplary acid salts include hydrochloride, hydrobromide, orthophosphate, benzoate, maleate, tartrate, succinate, citrate, salicylate, sulfate, acetate, and the like. Mixtures are operable.

The precise mechanism of the group of ACE inhibitors in stimulating angiogenesis is unknown. Moreover, it is unknown whether the ACE inhibitors influence angiogenesis directly or by interacting with other angiogenic agents. While not intending to be bound by any particular theory, it is proposed that the ability of nonsulfhydryl ACE inhibitors, like quinapril, to stimulate angiogenesis in an ischemic situation may be mediated through bradykinin-mediated increased NO production by the remaining healthy endothelial cells in the ischemic zone.

Angiogenesis is defined in adult organism as the formation of new blood vessels by a process of sprouting from pre-existing vessels. This neovascularization involves activation, migration, and proliferation of endothelial cells and is driven by several stimuli, among those shear stress. Among effects of ACE inhibition, suppression of Angiotensin II production, direct postsynaptic sympatholytic effect, acceleration of endothelium regrowth, and improvement in endothelial function lead to the observed increase in blood flow, which in turn increases shear stress, and potentially angiogenesis. On the other hand, cardiac capillary length density induced by ACE inhibition, was inhibited with Icatibant, a B2-receptor antagonist. Bradykinin is degraded by bradykininase II, an identical enzyme to ACE, and stimulates NO production via its receptor B2. Thus, ACE inhibition contributes to maintain bradykinin activity, and may increase NO production. The promotion of NO accumulation with ACE inhibitors (captopril, enalaprilat, ramipril) has been established in coronary microvessels using the Greiss reaction (*Circulation,* 95:176–182), and NO participation was strongly suggested in some beneficial effects of ACE inhibition treatment (*J. Clin. Invest.,* 100:678–684). Several studies support evidence that NO is crucial in VEGF-induced angiogenesis (*J. Clin. Invest.,* 99:2625–2634).

While the method of the present invention can be practiced in vitro, it has particular usefulness in in vivo applications. The present invention, therefore, includes the administration to an animal, particularly a human, of a therapeutically effective amount of at least one of the group of ACE inhibitors described above, as well as pharmaceutical compositions containing a therapeutically effective amount of the ACE inhibitors and a pharmaceutically acceptable carrier. A preferred embodiment of the present invention includes the administration of the ACE inhibitors, as well as the ACE inhibitor compositions to stimulate, including but not limited to induce or enhance, angiogenesis. The ACE inhibitors, as well as the ACE inhibitor compositions, may also be useful in the promotion of angiogenesis, such as in the promotion of wound healing, bone healing, and in the treatment of bums, as well as in promoting the formation, maintenance, and repair of tissue.

The ACE inhibitor-containing compositions of the present invention can be administered to a patient alone or as part of a composition that contains other components such as excipients, diluents, and carriers, all of which are well-known in the art. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

The final form of the pharmaceutical preparations made in accordance with the invention can vary greatly. Orally administrable forms, i.e., tablets, caplets, and capsules, are preferred. Solid, semi-solid, and liquid formulations can be made. However, solids are highly preferred. The optional excipients which can be used in the instant compositions are also substances which must be compatible with magnesium oxide so that it does not interfere with its function in the composition.

Compositions suitable for parenteral injection may comprise physiologically acceptable sterile aqueous or nonaqueous solutions, dispersions, suspensions, or emulsions and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), Cremophor EL (a derivative of castor oil and ethylene oxide; purchased from Sigma Chemical Co., St. Louis, Mo.) and suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, sodium carbonate, modified starch, polyvinylpyrrolidone (cross- or uncross-linked), and modified cellulose derivatives, (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; (i) lubricants, as for example, talc, hydrogenated vegetable oil, zinc stearate, calcium stearate, magnesium stearate, solid polyethylene glycols, sodium lauryl sulfate; () pigments; and (k) colorants or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, Cremophor EL (a derivative of castor oil and ethylene oxide; purchased from Sigma Chemical Co., St. Louis, Mo.), polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and, therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The above ACE inhibitor-containing compositions set forth above will be used in therapeutic amounts as indicated in the Physicians' Desk Reference (PDR) 47th Edition (1993), which is incorporated herein by reference, or such therapeutically useful amounts as would be known to one of ordinary skill in the art. In general, the dose of ACE inhibitor administered to an animal, particularly a human, in the context of the present invention should be sufficient to effect a therapeutic angiogenic response in the animal over a reasonable time frame.

The compositions can be administered at the recommended maximum clinical dosage or at lower doses. The dose will be determined by the strength of the particular ACE inhibitor employed and the condition of the animal, as well as the body weight of the animal to be treated. The size of the dose also will be determined by the existence, nature, and extent of any adverse side-effects that might accompany the administration of a particular compound. In determining the effective amount of the ACE inhibitor in the stimulation of angiogenesis, the physician need only evaluate the effects of the ACE inhibitor in the animal being treated by incrementally increasing the dosage in increments ranging from about 0.1 to about 20 mg/kg body weight to achieve as high a cumulative level of the ACE inhibitor in the animal as possible without adverse side effects being manifested. The ACE inhibitor will typically be adminstered to the animal being treated for a time period ranging from a day to a few weeks, consistent with the clinical condition of the treated animal. This dosage regimen will usually be within the range of about 0.1 to about 500 mg/kg body weight per day, although higher dosage amounts may be required in some situations.

An ACE inhibitor will be generally administered to a mammal, such as a human, in an amount of about 0.5 mg/kg to about 100 mg/kg of body weight per day. A suitable dose can be administered in suitable subdoses per day, particularly in a prophylactic regimen. The precise treatment level will be dependent upon the response of the animal, e.g., the human patient, being treated. To stimulate angiogenesis in a particular organ, the dose of the ACE inhibitor may be administered by a time-release pellet implanted in than organ. Preferably, the pellet will release the ACE inhibitor over a period of a few days, e.g., 2 days. Alternatively, a catheterization procedure may be used, whereby the ACE inhibitor is introduced by means of a catheter.

The desirable extent of the angiogenesis will depend on the particular condition or disease being treated, as well as the stability of the patient and possible side-effects. In proper doses and with suitable administration of certain compounds, the present invention provides for a wide range of development of blood vessels, e.g., from little development to essentially full development.

Methods of preparing the compositions of the present invention are known to those of skill in the art. While any techniques known to those of skill in the art for preparing ACE inhibitor-containing compositions can be employed, and several have been disclosed (U.S. Pat. Nos. 4,344,949, 4,374,829, and 4,425,355), and which are appropriate, a wet granulation process is preferred.

The percentages in which excipients are used are not critical. In general, their quantities will be consistent with the amount given above for the drug and stabilizer components (disintegrant about 1% to about 15% of the total composition; lubricant about 0.1% to about 5% of the total composition; and binder about 1% to about 10% of the total composition), i.e., they make up the remainder of the composition.

The drug preparations can be adapted for immediate, slow, or sustained release profiles, or any combination of these. Thus, a formulation adapted to give an initial loading dosage within 30 minutes followed by sustained release of the remaining drug over 4 to 12 hours is contemplated. Sustained and immediate release formulations are preferred.

Reasonable variations, such as those which would occur to a skilled artisan, can be made herein without departing from the scope of the invention.

All of the references cited herein are hereby incorporated in their entireties by reference.

EXAMPLES

The examples presented below are intended to illustrate particular embodiments of the invention, and are not intended to limit the scope of the specification or the claims in any way.

Example 1

Angiogenesis following resection of femoral artery was assessed at Day 10 (D10) and D40 post-operatively on functional (blood pressure ratio of ischemic to healthy limb, vasoreactivity and resistance) and morphological (angiography and capillary density) criteria. At D10, rabbits were randomly assigned either to be controls (n=6), to receive a single intra-arterial injection of VEGF (n=6), or a daily subcutaneous injection up to D35 of captopril (n=7) or quinaprilat (n=8). In both captopril or quinaprilat groups, residual ACE activity was equivalent in plasma (42.54±0.03% vs. 41.53±0.02%, p=ns), but not in tissue, where quinaprilat lowered ACE activity significantly (p<0.01) more frankly than captopril (13% vs. 61%). Both functional and morphological criteria disclosed an improvement in quinaprilat-treated rabbits, similar to the one in VEGF group, whereas captopril-rabbits did not develop their microvascular network to a higher degree than control group.

Based on the results, it was concluded that ACE inhibition with quinaprilat stimulates angiogenesis in vivo in rabbit ischemic hindlimb model. It is the opinion of the inventor that angiogenesis stimulation in ischemia is a property for nonsulfhydryl ACE inhibitors having a high tissue affinity, and that this property involves a compensatory production of nitric oxide in the ischemic region.

Methods

Animal Model

The animal model was a previously described rabbit ischemic hindlimb model (*J. Clin. Invest.* 93:662–670). A total of 42 New Zealand White rabbits (3.8–4.4 kg) (Pine Acre Rabbitry, Norton, Mass.) were anesthetized with a mixture of ketamine (50 mg/kg) and acepromazine (0.8 mg/kg) following premedication with xylazine (2 mg/kg). A longitudinal incision was then performed, extending from the inguinal ligament to a point just proximal to the patella. Through this incision, the femoral artery and each of its branches were dissected free along its entire length. After dissecting the popliteal and saphenous arteries distally, the external iliac artery and all of the above arteries were ligated with 4.0 silk (Ethicon, Sommerville, N.J.). Finally, the femoral artery was completely excised from its proximal origin as a branch of the external iliac artery, to the point distally where it bifurcates to form the saphenous and popliteal arteries. Following excision of the femoral artery, retrograde propagation of thrombus leads to occlusion of the external iliac artery. Blood flow to the ischemic limb consequently becomes dependent upon collateral vessels issuing from the internal iliac artery.

Study Design

Animals with limb ischemia were randomly divided into 4 groups. The VEGF group, as a positive control group, consisted of 6 rabbits to which 530 μg were administered intra-arterially at D10. The ischemic control group consisted of 6 rabbits receiving no medication of any kind. The captopril group (n=7) and the quinaprilat group (n=8) received one daily injection of captopril (25 mg) or quinaprilat (2 mg) using subcutaneous route, starting after the basal investigations on D10 and until D35.

The four groups were investigated at D10 and D40 post-operatively at which time lower limb blood pressure, vasomotor reactivity, and angiographic score were evaluated. All animals from each group were sacrificed on post-operative D40, and studied at necropsy.

An additional group of 15 rabbits underwent the ischemic limb operation, and were either non-treated (n=3), treated with captopril (n=7), or treated with quinaprilat (n=5) from D10 up to D35. Then, they were sacrificed, and muscles harvested for tissue in order to measure tissue ACE activity.

Measurement of Serum Levels of Angiotensin Converting Enzyme Activity

Serum ACE Activity

The serum ACE activity in the blood samples obtained from ear vein was determined using a kit obtained from Sigma (St. Louis, Mo.). The procedure used is a spectrophotometric method utilizing the synthetic tripeptide substrate N-[3-(2-furyl)acryloyl]-L-phenylalanylglycylglycine (FAPGG). ACE catalyzes hydrolysis of FAPGG to furylacryloylphenylalanine (FAP) and glycylglycine, which results in a decrease in absorbance at a wavelength of 340 nm. The ACE activity in the sample was determined by comparing the sample reaction rate to that obtained with an ACE calibrator.

In the two groups treated with either quinaprilat or captopril, ACE activity was measured in serum at D10 as basal value, at D 14 to assess the efficacy and equivalence of treatments, and at D40 to control the absence of residual effect after the five washout days. The efficiency of the treatment is calculated as the percentage of the D10 serum activity according to the ratio: D14 serum activity/D10 serum activity.

Tissue ACE Activity

In order to determine the tissue ACE activity, muscles from the additional group were harvested, weighed, and homogenized in PBS. The obtained solution was used as a substrate for the ACE determination kit (Sigma, St. Louis, Mo.), and the result, divided by sample weight, is expressed as international units per gram of tissue (UI/g).

Lower-limb Blood Pressure Ratio

For the above indicated in vivo physiologic studies performed at D10 or D40, each rabbit was anesthetized with ketamine (10 mg/kg) and acepromazine (0.2 mg/kg) following premedication with xylazine (2 mg/kg). Blood pressure was measured in both hindlimbs, on D10 and D40. On each occasion, the hindlimbs were shaved and cleaned, the pulse of the posterior tibial artery was identified with a Doppler probe, and the systolic blood pressure in each limb was measured using standard techniques. The blood pressure ratio was defined for each rabbit as the ratio of systolic pressure of the ischemic limb to the systolic pressure of the normal limb.

Vasomotor Reactivity and Vascular Resistance

After measurement of lower limb blood pressure, a 3 Fr., end-hole infusion catheter (Tracker-i 8 TM, Target Therapeutics, San Jose, Calif.) was inserted into the left common carotid artery and advanced to the abdominal aorta. A 0.018 inch Doppler guidewire (Cardiometrics, Inc., Mountain View, Calif.) was advanced through the 3 Fr. infusion to the proximal segment of the internal iliac artery supplying the ischemic limb. The Doppler wire records a real-time, spectral analysis of the Doppler signal, from which the average peak velocity (APV, the temporal average of the instantaneous peak velocity wave form) was calculated and displayed on line.

A second catheter (Tracker-18 TM) was introduced into the left common carotid artery through the same cutdown and advanced to the origin of the common iliac artery of the ischemic limb using a separate 0.018 inch guidewire (Hi-Torque Floppy II, Advanced Cardiovascular Systems, Temecula, Calif.) under fluoroscopic guidance. This catheter was used for infusion of vasoactive drugs, for measurement of intra-arterial blood pressure via connection to a pressure transducer, and for selective angiography of the ischemic limb (see below). The use of this catheter for drug infusion precluded graphic display of the blood pressure during drug infusion; intra-arterial blood pressure was therefore determined immediately following intra-arterial drug infusion before the angiogram was made.

The vasodilators, acetylcholine chloride, sodium nitroprusside (endothelium-independent), and serotonin creatine sulfate were administered intra-arterially over 2 minutes via a constant infusion pump (1 mL/min). Each was administered at a dose of 1.5 μg/min/kg on D10 and on D40. A lag of 5 minutes was allowed between each drug in order to return to basal hindlimb blood flow values.

Calculation of Vascular Reactivity

Vascular reactivity was assessed in this study measuring the variation of blood flow induced by vasodilators in the internal iliac artery of the ischemic limb. Blood flow was calculated from the Doppler measurements, using the formula $Q_D=(\pi d^2/4)(0.5 \times APV)$, where $Q_D$=Doppler-derived time average flow, d=vessel diameter, and APV=time average of the spectral peak velocity (*Am. J Physiol.,* 1994;267:H1263-H1271). The mean velocity was estimated as 0.5×APV by assuming a time-averaged parabolic velocity profile across the vessel. The Doppler-derived flow calculated in this way has been shown to correlate with flow measurements determined by electromagnetic flow meters both in vitro and in vivo (*Am. J Physiol.*, 1994;267:H1263-H1271). The angiographic diameter of main collateral artery was determined using an automated edge-detection system that has been previously validated in vivo (*Am. J Physiol.*, 1994;267:H1263-H1271). The film selected for analysis was scanned with a high resolution video camera; the signal produced by the video camera was digitized and displayed on a video monitor. Center-lines were traced manually for a 10-mm long segment beginning immediately distal to the tip of the Doppler wire. The contours were subsequently detected automatically on the basis of the weighted sum of first and second derivative functions applied to the digitized brightness information. The vascular diameter was then measured at the site of the Doppler sample volume, i.e., 5 mm distal to the wire tip (*Am. J Physiol.*, 1994;267:H1263-H1271). Cross-sectional area was calculated assuming a circular lumen.

Angiography was performed immediately after drug administration and intra-arterial blood pressure recording, using 1 mL of contrast media (RenoCal-76, Squibb Diagnostics, New Brunswick, N.J.).

The results of calculation for blood flow are expressed as the ratio of blood flow after vasodilator injection to basal blood flow, measured just before the injection.

Calculation of Vascular Resistance

The vascular resistance was calculated using this formula: $R_i = P_c/Q_D$ (where $R_i$=vascular resistance at internal iliac artery, $P_c$=blood pressure at common iliac artery). The results of calculation for vascular resistance are expressed as the ratio of resistance after vasodilator injection to basal resistance, measured just before the injection.

Angiographic Score

On post-operative D10 and D40, angiograms of whole media thigh lesion were performed at a rate of 1 film per second for 10 seconds, using 5 mL of contrast media injected with an automated angiographic injector (Medrad, Pittsburgh, Pa.) at a rate of 1 mL/sec. Serial images of the ischemic limb were recorded on 105-mm spot film at a rate of 2 films per second for 4 seconds.

For quantitative analysis of collateral development ("angiographic score"), a composite of 5-mm$^2$ grids on the 4-second angiograms was placed over the medial thigh area. The total number of grid intersections in the medial thigh area (A), as well as the number of intersections crossed by a contrast-opacified artery (B), were counted by a single observer blinded to the treatment regimen. An angiographic score was calculated for each film as the ratio B/A.

Capillary Density

The impact of ACE inhibitors administration on microscopic angiogenesis was assessed by measuring the number of capillaries in light microscopic sections taken from the ischemic hindlimb. Tissue specimens obtained as transverse sections from the adductor muscle, the semi-membranous muscle, and the quadriceps of both limbs of each animal at the time of sacrifice (D40) were embedded in O.C.T. compound (Miles, Elkhart, Ind.) and snap-frozen in liquid nitrogen. Multiple 5-em thick frozen sections were then cut from each specimen on a cryostat (Miles). The tissue sections were stained for alkaline phosphatase with an indoxyl-tetrazolium method to detect capillary endothelial cells as previously described (Cardiovascular Research, 1984; 18:724–732; *J. Vasc. Surg.*, 1992;16:181–191) and counter-stained with eosin. Capillaries were counted under a 10X objective to determine the capillary density (mean number of capillaries/mm$^2$). Twenty-one different fields from the 3 muscles were randomly selected for the capillary counts.

Drugs

Recombinant human VEGF protein (rhVEGF$_{165}$) was the generous gift of Dr. Bruce Keyt (Genentech, South San Francisco, Calif.). Quinaprilat (CI-928, Accupril®: ampoules, 1 mg/1 mL), the active diacid of quinapril, was generously provided by Parke-Davis (Ann Arbor, Mich.) and captopril (Capoten®: tablets of 12.5 mg) from Bristol Meyers/Squibb (Princeton, N.J.). In a preliminary experiment, the dose was determined for both drugs in order to induce the same level of serum ACE inhibition. A 50% to 60% inhibition was achieved in ischemic rabbits with 2 mg of quinaprilat (=2 mL) or 25 mg of captopril, both using subcutaneous route. For the latter drug, tablets were daily dissolved in saline serum and the resulting suspension was injected. Acetylcholine chloride, serotonin creatine sulfate, and sodium nitroprusside were all purchased from Sigma Chemical Co., St. Louis, Mo.

Statistical Analysis

All results are expressed as mean ±standard error (m±SEM). The multiple comparison between the four groups was performed by an ANOVA analysis. When a significant difference was detected, unpaired Student's t-test was used for comparisons between two means. A value of $p<0.05$ was interpreted to denote statistical significance.

Results

Effect of Daily Treatment With ACE Inhibitors in Rabbits

Serum ACE activity

The residual ACE activity in the serum for both captopril and quinaprilat groups was identical at D14 (Table 1, below), respectively 42.54±0.03% versus 41.53±0.02% (p=0.78). This magnitude of inhibition was measured at 24 hours, right before the following injection, which denotes an ACE inhibition higher than 50% at any time. After 5 days of discontinuation of injections, i.e., at D40, the serum exhibited a value close to normal for ACE activity in captopril (92.87±0.04%) and quinaprilat (80.71±0.08%) groups (FIG. 1).

Tissue ACE activity

Mean tissue activity in thigh muscles from additional rabbits were significantly different between the three groups (ANOVA: p<0.01), reaching 12.65±2.60 Ul/g in control group, 7.65±1.69 Ul/g in captopril group (p=0.14 vs. controls), and 1.69±0.70 Ul/g for quinaprilat-treated rabbits (p<0.05 vs. controls); that corresponds to a residual activity respectively of 13% (for quinaprilat) vs. 61% (for captopril) of the non-treated tissue activity (FIG. 1).

Lower limb calf blood pressure ratio

VEGF and quinaprilat induced a better recovery of ischemic/normal calf blood pressure ratio than observed in the control and in the captopril group. At D40, the blood pressure ratio in VEGF group was 0.74±0.03, compared to 0.45±0.04 for control group (p<0.01). The value in quinaprilat group was 0.86±0.03 (p<0.01), but only 0.47±0.05 in the captopril-treated rabbits (FIG. 2). No statistical difference was found between VEGF and quinaprilat groups, neither between captopril and control groups.

Vasomotor reactivity and vascular resistance in collateral development

Ten days after removal of the femoral artery, the vascular response to vasodilators did not exhibit significant differences between the four groups. The mean value of the blood flow ratio (stimulated flow/basal flow) calculated upon the 27 rabbits shows a moderate dilation induced by acetylcholine or nitroprusside (1.64±0.01 and 1.69±0.01). Serotonin induced a dramatic reduction in blood flow, equivalent in the four groups (mean value of the flow ratio: 0.37±0.04), which reflects an intense vasoconstriction.

At D40 (FIG. 3), the response to acetylcholine was improved in each group, but with significant differences in magnitude (ANOVA: p<0.01); the response in the control and captopril groups limited within a moderate increase in flow ratio (1.74±0.09 and 1.93±0.07) whereas responses in VEGF and quinaprilat elicited a much higher vasodilatation (2.72±0.22 and 3.06±0.25). Comparisons to control group showed a statistical difference for VEGF and quinaprilat (p<0.01), but not for captopril (p=0.09) group. The responses to nitroprusside resulted in the same pattern, i.e., a significant higher vasodilatation in VEGF (2.66±0.35, p<0.05) and quinaprilat groups (2.94±0.24, p<0.05), not for captopril (2.05±0.11, p=ns), compared to control group (1.81±0.09). After serotonin, the blood flow still decreased in control and captopril groups (0.63±0.09 and 0.62±0.05), but increased in VEGF and quinaprilat groups (1.19±0.09 and 1.17±0.08, p<0.01 vs. control for both).

The vascular resistance at D10 was comparable between the four groups after vessel stimulation with acetylcholine, nitroprusside, or serotonin (Table 1). Conversely, the sequences of vascular resistance (FIG. 4) at internal iliac artery had definite distinction between the four groups at D40 (ANOVA: p<0.01). The degree of resistance decrease in control and captopril groups recorded significantly less than VEGF and quinaprilat in response to acetylcholine (0.57±0.04 and 0.51±0.03 vs. 0.35±0.03 and 0.32±0.03; p<0.01 vs. control for both VEGF and quinaprilat groups) or nitroprusside (0.42±0.02 and 0.38±0.03 vs. 0.29±0.04 and 0.28±0.02; p<0.05 for VEGF and p<0.01 for quinaprilat). Finally, the severe increase in resistance induced by serotonin at D10 was reversed only in VEGF and quinaprilat groups (0.77±0.04 and 0.94±0.06; p<0.05 vs. control for both) and persisted attenuated in control and captopril groups (2.15±0.59 and 1.88±0.20). Angiographic Assessment of Collateral Formation The angiographic score (FIG. 5) at D40 in VEGF group (50.88±0.04%, p<0.01) and in quinaprilat group (51.19 0.02%, p<0.01) recorded significantly higher than these in control group (33.66±0.02%) and captopril group (35.03±0.02%, p=ns).

Histological Assessment of Angiogenesis

Figure 5A:
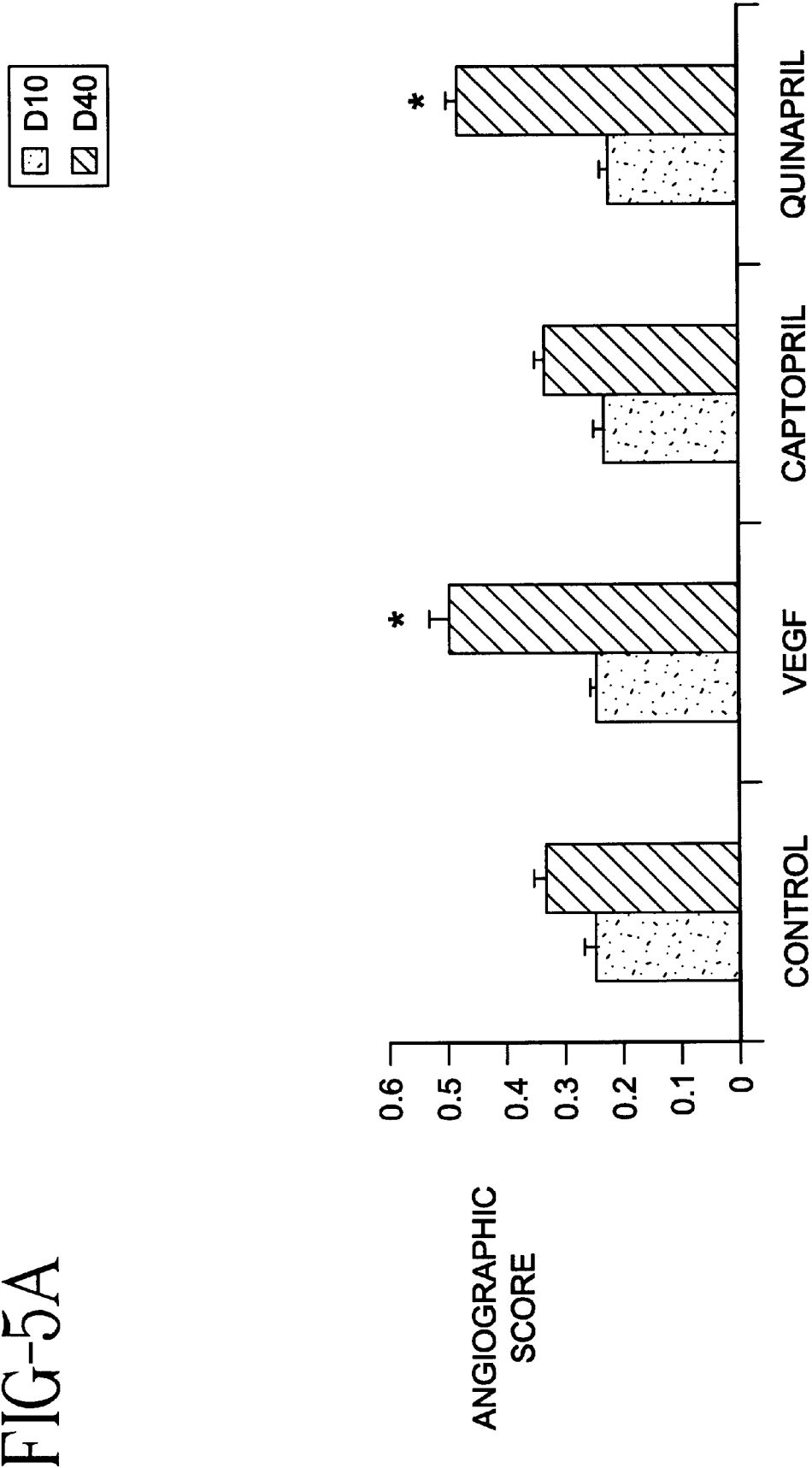
FIG. 5. Bar graphs (FIGS. 5A and 5B) of angiographic score (A) and capillary density (B) at D10 and D40. Values are means ±SEM. The ANOVA difference between the four groups for angiographic score ($p<0.01$) and for capillary density ($p<0.01$) is due to a significant (*=$p<0.01$) difference between VEGF and control rabbits, and between quinaprilat and control animals. These quantitative analysis of collateral development in media thigh lesion assess more developed angiogenesis after VEGF or quinaprilat administration than in control or captopril rabbits.
Figure 5B:
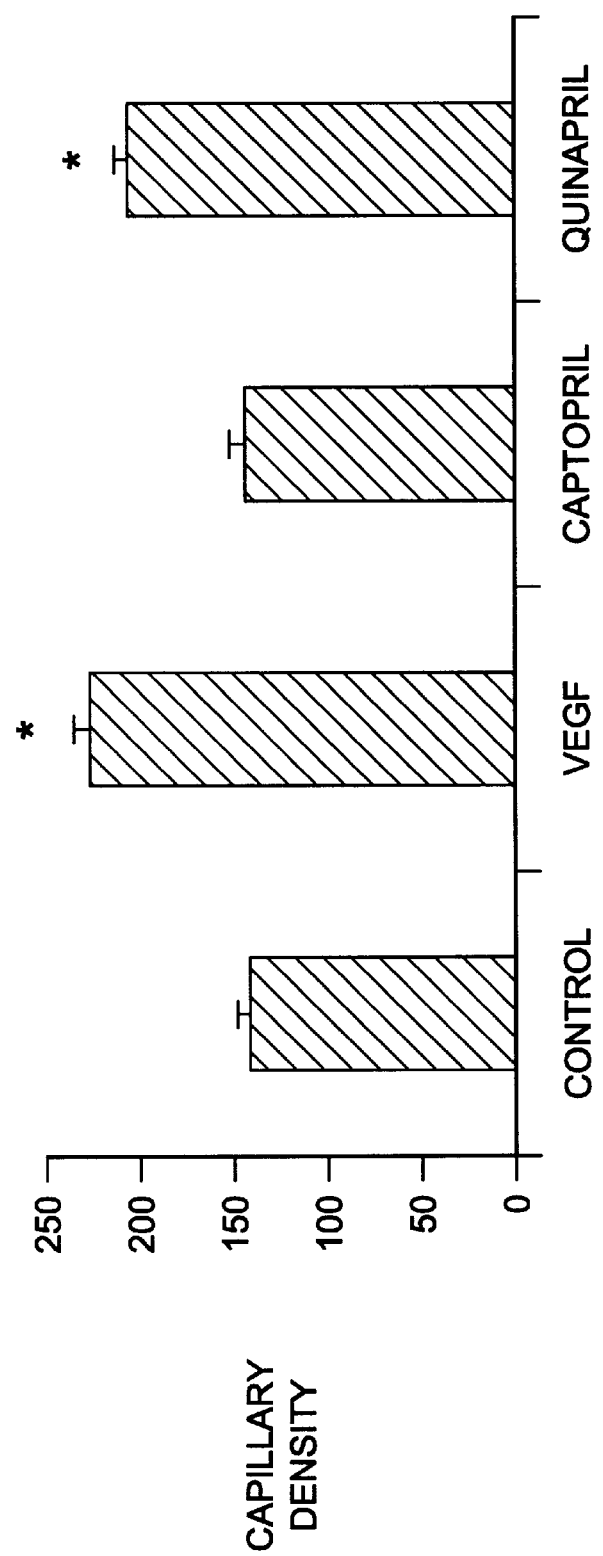

The histological evaluations of the medial thigh muscles in the ischemic limbs on D40 showed prominent increase of capillary formation in VEGF- and quinaprilat-treated animals (FIG. 5). The capillary density in VEGF group (228.8±9.6/mm$^2$, p<0.01), as well as quinaprilat group (214.0±6.4/mm$^2$, p<0.01) was significantly higher than in control group (140.5±4.26/mm$^2$) and in captopril group (147.2±11.9 mm$^2$).

TABLE 1

Basal Data of Rabbits

| Group | Day | Serum ACE Activity (U/L) | Body Weight (kg) | SBP at Healthy Limb (mmHg) | Rest Blood Flow (mL/min) | Rest Vascular Resistance |
|---|---|---|---|---|---|---|
| Control | 10 | | 4.15 ± 0.07 | 96.9 ± 2.4 | 15.38 ± 0.64 | 4.21 ± 0.11 |
| (n = 6) | 40 | | 4.02 ± 0.18 | 124.5 ± 2.5 | 19.19 ± 0.31 | 3.44 ± 0.05 |
| VEGF | 10 | | 4.08 ± 0.06 | 85.3 ± 1.8 | 14.78 ± 0.48 | 3.95 ± 0.11 |
| (n = 7) | 40 | | 4.01 ± 0.08 | 92.2 ± 2.7 | 14.32 ± 0.77 | 4.46 ± 0.21 |
| Captopril | 10 | 55.94 ± 0.75 | 4.17 ± 0.13 | 89.7 ± 2.2 | 15.03 ± 0.38 | 3.69 ± 0.10 |
| (n = 7) | 14 | 23.92 ± 0.60 | | | | |
| | 40 | 51.80 ± 0.80 | 4.39 ± 0.13 | 126.0 ± 3.6 | 16.04 ± 0.19 | 3.93 ± 0.07 |
| Quinaprilat | 10 | 59.50 ± 1.38 | 4.19 ± 0.10 | 99.5 ± 1.3 | 14.37 ± 0.32 | 4.63 ± 0.19 |
| (n = 8) | 14 | 24.32 ± 0.46 | | | | |
| | 40 | 46.40 ± 0.98 | 4.54 ± 0.20 | 117.1 ± 1.7 | 13.87 ± 0.48 | 5.47 ± 0.18 |

The body weight and basal hemodynamic data at Days 10 and 40 are reported for reference groups (control and VEGF) and ACE inhibitor groups (captopril and quinaprilat). The ACE activity is also displayed at Days 10, 14, and 40 for ACE inhibitor-treated groups. ANOVA test displayed no significant different in body weight, SBP (systolic blood pressure) at healthy hindlimb, rest blood flow, and rest vascular resistance between the 4 groups, respectively, at Days 10 and 40. This test was also not significant for comparison of serum ACE activity between captopril and quinaprilat groups respectively at Day 10 (basal value), Day 14 (efficiency value), and Day 40 (5 days after discontinuation).

Discussion

The results of the study demonstrated the ability of a nonsulfhydryl ACE inhibitor, quinaprilat, to stimulate angiogenesis in an ischemic situation. Specifically, the results of the study establish that inhibition of ACE stimulates angiogenesis in this rabbit ischemic model with quinaprilat, in the same extent as VEGF, but also that this result was not valid for captopril, another ACE inhibitor. The systematic quantification of angiographic recordings (angiographic score), assessed that development of angiographically visible collateral arteries in quinaprilat- and VEGF-treated animals exceeded that in control and captopril groups. The necropsy examination confirmed these data, documenting a comparable increase in vascularity at the capillary level in quinaprilat and VEGF groups. These results may have clinical implications for patients suffering peripheral artery disease.

While this invention has been described with an emphasis on preferred embodiments, it will be obvious to those of ordinary skill in the art that variations in the preferred method and pharmaceutical compositions may be used and that it is intended that the invention may be practiced otherwise than as specifically described herein. Accordingly, this invention includes all modifications encompassed within the spirit and scope of the invention as defined by the following claims.

What is claimed is:

1. A method of stimulating angiogenesis in a mammal, which method comprises administering to a mammal in need thereof at least one ACE inhibitor conforming to the general formula:

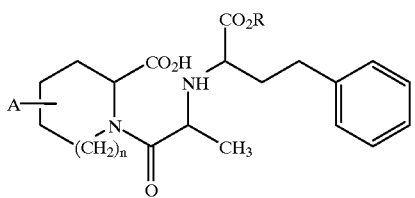

wherein A is absent, a fused 5-, 6-, or 7-membered cycloaliphatic ring or a fused benzene ring which is unsubstituted or substituted by 1 or 2 alkoxy groups having 1 to 4 carbon atoms; n is 0 or 1, and R is hydrogen or alkyl having 1 to 5 carbon atoms; in an amount effective to stimulate angiogenesis.

2. The method of claim 1, whereby the method is for inducing or enhancing angiogenesis.

3. The method of claim 1, whereby A is absent, a fused 5- or 6-membered cycloaliphatic ring or a fused benzene ring which is unsubstituted or substituted by 2 methoxy groups; n is 0 or 1, and R is hydrogen or ethyl.

4. The method of claim 1, whereby the ACE inhibitor is quinapril or quinaprilat.

5. The method of claim 1, whereby the mammal is human.

6. The method of claim 1, whereby the ACE inhibitor is administered in an amount ranging from about 1 mg to about 80 mg per dose.

7. The method of claim 1, whereby the ACE inhibitor is administered in a composition comprising an ACE inhibitor and a pharmaceutically acceptable carrier.

8. The method of claim 1, whereby the method comprises promotion of wound healing, bone healing, or the treatment of burns.

9. The method of claim 1, whereby the method comprises vascularization of synthetic skin grafts.

10. The method of claim 1, whereby the method comprises enhancement of collateral circulation.

11. A method of stimulating angiogenesis in a mammal, which method comprises administering to a mammal in need thereof quinapril or quinaprilat in an amount effective to stimulate angiogenesis.

12. The method of claim 11, whereby the mammal is human.

13. The method of claim 11, whereby the quinapril is administered in an amount ranging from about 1 mg to about 80 mg per dose.

14. The method of claim 11, whereby the quinapril is administered in a composition comprising the quinapril or quinaprilat and a pharmaceutically acceptable carrier.

15. The method of claim 11, whereby the method comprises promotion of wound healing, bone healing, or the treatment of burns.

16. The method of claim 11, whereby the method comprises vascularization of synthetic skin grafts.

17. The method of claim 11, whereby the method comprises enhancement of collateral circulation.

* * * * *

UNITED STATES PATENT AND TRADEMARK OFFICE
CERTIFICATE OF CORRECTION

PATENT NO. : 6,191,144 B1
DATED : February 20, 2001
INVENTOR(S) : Jeffery Michael Isner It is certified that error appears in the above-identified patent and that said Letters Patent is hereby corrected as shown below:

<u>Title page,</u>
ABSTRACT, line 10, "bums" should read -- burns --.

<u>Claim 8,</u>
Line 3, "bums" should read -- burns --.

Signed and Sealed this

Sixteenth Day of April, 2002

Attest:

JAMES E. ROGAN
*Director of the United States Patent and Trademark Office*

*Attesting Officer*